United States Patent
Grass et al.

(10) Patent No.: US 9,275,454 B2
(45) Date of Patent: Mar. 1, 2016

(54) MOTION COMPENSATED SECOND PASS METAL ARTIFACT CORRECTION FOR CT SLICE IMAGES

(71) Applicant: KONINKLIJKE PHILIPS N.V., Eindhoven (NL)

(72) Inventors: Michael Grass, Buchholz in der Nordheide (DE); Holger Schmitt, Luetjensee (DE); Dirk Schafer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 15 days.

(21) Appl. No.: 14/350,377

(22) PCT Filed: Oct. 22, 2012

(86) PCT No.: PCT/IB2012/055799
§ 371 (c)(1),
(2) Date: Apr. 8, 2014

(87) PCT Pub. No.: WO2013/061239
PCT Pub. Date: May 2, 2013

(65) Prior Publication Data
US 2014/0270450 A1    Sep. 18, 2014

Related U.S. Application Data

(60) Provisional application No. 61/550,509, filed on Oct. 24, 2011.

(51) Int. Cl.
| G06K 9/00 | (2006.01) |
|---|---|
| G06T 7/00 | (2006.01) |
| A61B 6/03 | (2006.01) |
| A61B 6/00 | (2006.01) |
| A61B 6/12 | (2006.01) |
| G06K 9/62 | (2006.01) |
| G06T 5/00 | (2006.01) |
| G06T 11/00 | (2006.01) |

(52) U.S. Cl.
CPC ............. *G06T 7/0012* (2013.01); *A61B 6/032* (2013.01); *A61B 6/12* (2013.01); *A61B 6/5241* (2013.01); *A61B 6/5264* (2013.01); *G06K 9/6201* (2013.01); *G06T 5/00* (2013.01); *G06T 11/008* (2013.01); *A61B 6/503* (2013.01); *A61B 6/541* (2013.01)

(58) Field of Classification Search
None
See application file for complete search history.

(56) References Cited

U.S. PATENT DOCUMENTS

| 6,721,387 | B1* | 4/2004 | Naidu | A61B 6/032 378/4 |
|---|---|---|---|---|
| 9,052,403 | B2* | 6/2015 | Morton et al. | |
| 2008/0247624 | A1* | 10/2008 | Scholz | A61B 6/5258 382/131 |
| 2009/0074278 | A1* | 3/2009 | Beaulieu | A61B 6/032 382/131 |
| 2009/0163798 | A1* | 6/2009 | Abbott | A61B 5/04004 600/410 |
| 2010/0183214 | A1* | 7/2010 | McCollough | A61B 6/032 382/131 |
| 2011/0007956 | A1* | 1/2011 | Meyer | A61B 6/032 382/131 |
| 2011/0081071 | A1* | 4/2011 | Benson | A61B 6/5258 382/154 |

FOREIGN PATENT DOCUMENTS

| WO | 2009091200 A2 | 7/2009 |
|---|---|---|
| WO | 2010076676 A1 | 7/2010 |

OTHER PUBLICATIONS

Aootaphao, S., et al.; Penalized-Likelihood Reconstruction for Metal Artifact Reduction in Cone-Beam CT; 2008; IEEE EMBS Conference; pp. 2733-2736.

* cited by examiner

Primary Examiner — Shervin Nakhjavan

(57) ABSTRACT

An apparatus and a method for correcting a CT slice image for an image artifact (330) caused by the motion of a high attenuation part (140) in an object (135) of interest. The CT slice image is based on projection images (310a,b). The apparatus and method uses a footprint (315a,b) of the part in each of the projection images (310a,b).

20 Claims, 5 Drawing Sheets

MOTION COMPENSATED SECOND PASS METAL ARTIFACT CORRECTION FOR CT SLICE IMAGES

CROSS REFERENCE TO RELATED APPLICATIONS

This application is a national filing of PCT application Ser. No. PCT/IB2012/055799, filed Oct. 22, 2012, published as WO 2013/061239 A2 on May 2, 2013, which claims the benefit of U.S. provisional application Ser. No. 61/550,509 filed Oct. 24, 2011, which is incorporated herein by reference.

FIELD OF THE INVENTION

The invention relates to an apparatus for correcting a cross sectional slice image for an image artifact, to a method of correcting a cross sectional slice image for an image artifact, to a medical image processing system for correcting a cross sectional slice image for an image artifact, to computer product and to a computer readable medium.

BACKGROUND OF THE INVENTION

An increasing number of patients who undergo a cardiac CT (computed tomography) examination have metallic implants in their hearts, such as artificial heart valves, biventricular pacemakers, stents, Amplatzer devices or similar. Prospectively gated cardiac CT scanning delivers good image results for soft tissue because the scans are carried out during the cardiac resting phase to so minimize motion-caused image artifacts. Unfortunately, small but non-negligible motion of the metallic implant inside the gating window may still lead to image artifacts. A cardiac computer tomography system is disclosed in Applicants' WO 2007060572.

SUMMARY OF THE INVENTION

It is an object of the present invention to provide an alternative apparatus and method to correct for an artifact in CT slice images.

The object of the present invention is solved by the subject matter of the independent claims wherein further embodiments are incorporated in the dependent claims.

It should be noted that the following described aspects of the invention equally apply to the method of correcting a slice image for an image artifact as well as to the medical image processing system for correcting cross sectional slice images for image artifacts, to the computer program element and to the computer readable medium.

According to a first aspect of the invention an apparatus for correcting a cross sectional slice image for an image artifact is provided. The slice image is based on CT projection images taken previously of an object at different times and taken at different angles whilst a high attenuation part of the object is in motion, thereby causing the artifact in the image. The apparatus comprises an input unit, a processing unit and an output unit. The input unit is configured to receive the to-be-corrected slice image and is configured to access the CT projection images. The processing unit comprises a segmenter unit ("segmentor"), an identifier unit ("identifier"), a matcher unit ("matcher"), an interpolator unit ("interpolator"), and an slice image reconstructor unit (image reconstructor).

The segmenter is configured to segment in the slice an artifact region.

The identifier is configured to use the so segmented artifact region to identify in each of a plurality of the CT projection images a footprint corresponding to the artifact region.

The matcher is configured to match, in each of the plurality of CT projection images, the identified footprint in the CT projection image to a matching footprint in that CT projection image. The matching footprint represents the part's position at acquisition time of that CT projection image.

The interpolator is configured to generate, for each of the plurality of CT projection images, an interpolated CT projection image by using the matching footprint in the CT projection image as a constraint for the interpolation in that CT projection image to so obtain a plurality of interpolated CT projection images.

The image reconstructor is configured to use the plurality of interpolated CT projection images to reconstruct a corrected version of the slice image.

The output unit configured to output the corrected version of the slice image.

The corrected slice image was previously reconstructed from the CT projection images obtained in a scan run by a CT scanner system.

The high attenuation part has a higher attenuation coefficient for the radiation (for example X-ray) used by the CT scanner than the average attenuation coefficient of the remainder of the object. An example is a metal part imbedded in organic soft tissue, such as a heart going through its cardiac cycles thereby moving about a catheter guide wire or an artificial heart valve residing in the heart during the scan.

However this is an example only and the invention may be used for any other object having a high attenuation part that changes position or orientation during a CT image acquisition run.

The CT projection images can be thought of as "source images" for the "target" image formed by the slice. The apparatus according to the invention operates principally at the source image level rather than the slice image level.

The image artifact in the previously reconstructed slice image is a result of the reconstruction algorithm used and the motion of the high attenuation part during the acquisition epoch of the CT projection images. Because the apparatus operates principally at the source image level, that is, on the CT projection images, a more thorough correction can be obtained because the apparatus operates at a level where the distortions and blurs are generally less pronounced as compared to distortions and blurs in the slice image. Rather than looking at metallic artifacts ("metallic shadows") in the slice image as a mere nuisance, the apparatus harnesses the information provided by the image artifact itself to obtain correction images at high fidelity. The artifact can be thought of as an image representation of a "reconstructed mean position" of the metallic object, that is, an "image" of a time average over the part's different positions during the acquisition epoch of the CT projection images. The artifact region defines a "swath" swept out by the different positions the part was assuming during the acquisition epoch.

Each of the projection images was acquired at a specific acquisition time and at a specific projection angle by the CT scanner.

Each of the matching footprints in any individual ones of the CT projection images represents the projection of the part in a "true" instantaneous position at the specific acquisition time. In contrast, the "in-image position" of the metal part in the slice image as represented by the segmented artifact region is an apparent "metal object area". The identification of the artifact region's footprint at projection image level is effected in one embodiment by forward projection which is the inverse operation to backward projection used in the previous first pass reconstruction of the slice image from the CT projection images.

The matching footprints encoding the true positions are found by the matcher at the projection image level by using the shape of the footprint of the forward projected reconstructed artifact region from the slice image level.

The artifact region includes the slice image regions representing the metal part but may also include voxel regions not representing the metal part proper but being pure artifacts such as streaks, blurs and distortion caused by the reconstruction algorithm and the motion of the metal part during the projection image CT acquisition epoch. According to one embodiment, the segmenter is so configured to confine segmentation to voxel regions representing the metal part proper.

In one embodiment the segmentation may comprise sub-regions that are not connected, that is, for any pair of points inside the segmentation, a path joining the pair may then not remain for all its length inside the segmented region.

In yet another embodiment, segmenter enforces rendering of "connected regions" only, that is, any pair of points inside the segmentation can be joined by a path, the path remaining for all its length inside the segmented region.

According to one embodiment, the artifact region in the slice image or in the new slice image represents a mean position over time of the part during its motion and whilst the CT projection images are acquired, the artifact region being the result of a previous reconstruction from the CT projection images of the slice image or the new slice image.

In one embodiment, a registration process on the projection images is effected and the displacement of the footprint of the artifact or metal shadow in each of the projection images with respect to the forward projected mean metal shadow footprint is estimated. In the registration process the geometric shape of the forward projected metal shadow is used to regularize the registration. The "true" positions of the moving part as encoded by the matching footprints found by the matcher are then used in a second pass reconstruction to so obtain the corrected version of the slice image.

According to one embodiment, the plurality of interpolated CT projection images are generated by replacing, in each of the plurality of CT projection images, image information inside the matching footprint in that CT projection image by interpolated image information. The interpolated image information is either obtained by using average image information (pixel values) outside the footprint to so essentially average out the footprint of the wire and to produce corrected slice image where no wire is visible. The pixel information for surrounding tissue is then used and the selected image will appear to the user as if it had never contained any metallic part in the first place. In another embodiment the opposite is achieved namely a better view at a corrected contrast of the metallic part embedded in the surrounding tissue is sought after. The corrected contrast may be achieved by replacing the interpolated pixels with higher or lower pixel values than the pixel values outside each of the matching footprints. In this case, the image information inside the matching footprints is manipulated and replaced by corrected intensity values for better contrast. In the reconstruction, the Hounsfield-scale is used.

According to one embodiment, upon user request and prior to the interpolation and the reconstruction of the corrected image, a new slice image is generated for feeding back, as input, into the apparatus. The reconstructor is configured to reconstruct the new slice image based on the plurality of matching footprints, thereby compensating for the part's motion during acquisition of the CT projection images. The input unit then receives the newly reconstructed and motion compensated slice image and the processing unit then starts over and processes the newly reconstructed slice image instead of the previous slice image.

In other words pre-processing step to pre-process the slice images is implemented according to one embodiment to obtain new slice images which is then used for feeding back as input into the apparatus and processed instead of the previous slice image. Corrected contrast representation with less blur of the artifact region can thereby be obtained.

The apparatus then uses this new corrected contrast slice image as input and processes it to obtain a better again at corrected contrast corrected version of the slice image.

In one embodiment the new slice image is output as the final output thereby by-passing the interpolator.

The image reconstructor in the apparatus can be a dedicated image reconstructor however in other embodiments the image constructor used previously to obtain the slice image may be also used to execute the reconstruction. In that case the apparatus would contain suitable API's and interface means to interface with the native image reconstructor system. Suitable re-programming and configuring of the native image reconstructor may then be needed.

In sum, the apparatus in one embodiment provides a motion-compensated second pass metal artifact reduction scheme.

In one embodiment the apparatus is applied to prospectively gated cardiac image acquisitions. The apparatus reduces artifacts in cardiac scan images when metal objects remain in motion inside the gating window. The apparatus may also be applied in interventional CT procedures to correct artifacts due to moving needles or catheters. It is understood that the invention is not restricted to heart CT imaging or metallic objects but the invention can be practiced with respect to any anatomical or non-anatomic object including highly attenuating singularities, where the part is moving during the CT acquisition epoch.

DEFINITIONS

The term "image artifact" or "metal shadow" includes blurs, streaks and distortions as presented to the observer of the slice image.

"footprints" are pixel regions representing the projections of either the part or the forward projected (function) image of the artifact.

"segmentation" is a region of voxels or pixels that together define in the image plane an object. Each pixel or voxel in the image plane can then be said to be either inside the object or outside the object. The segmentation also defines an outer contour, boundary and hence a "shape" of the object.

"Motion" or "change of position" of the metal object includes any rigid transformation thereof, that is, a rotation and/or a translation of the object as far as the change of position is discernable in the projection image. A projection of the part's motion can be expressed as an in-plane rigid transformation across the projection image plane of the part's footprint.

BRIEF DESCRIPTION OF THE DRAWINGS

Exemplary embodiments of the invention will be described in the following with reference to below drawings in which.

DETAILED DESCRIPTION OF EMBODIMENTS

Figure 1:
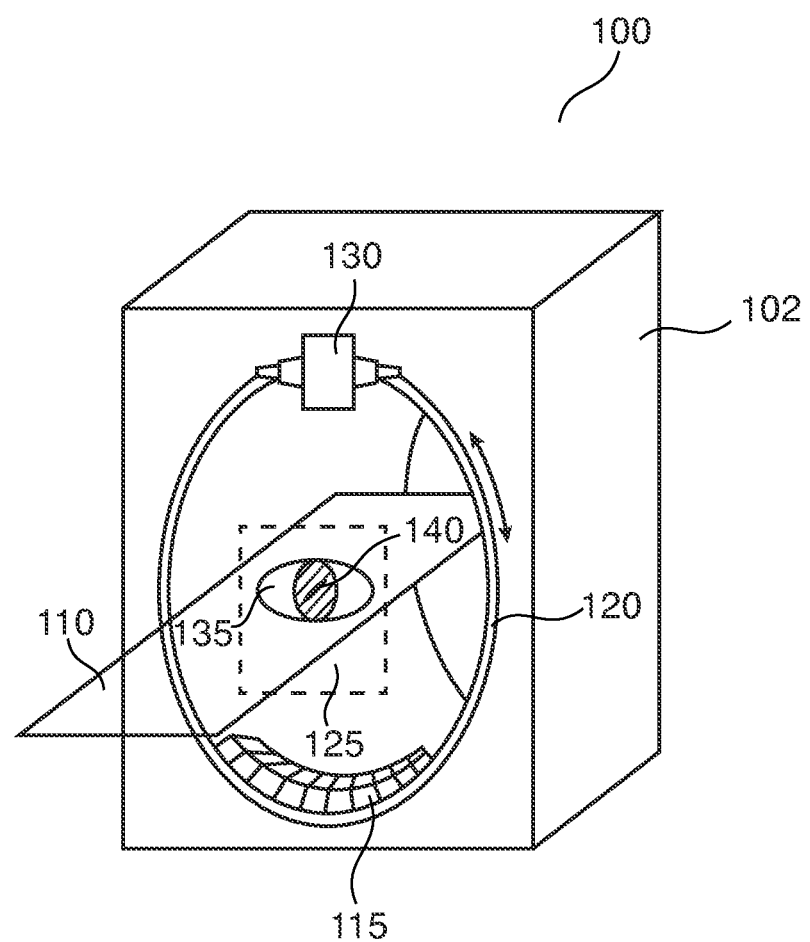
FIG. 1 shows a perspective view of a CT scanner system.

With reference to FIG. 1, an exemplary CT scanner system ("third generation") is shown. The system 100 comprises a frame 102 having a bore. A gantry 120 is rotatably arranged inside the bore as a rigid cylinder structure. Gantry 120 includes in rigid and opposed relationship an x-ray tube 130 and a detector array 115. An examination table 110 is provided extending into gantry 102 and passing through the center of gantry 120 cylinder. An object of interest such as a human heart 135 of a patient lying on the table 110 is positioned at the center point of gantry 120. Heart 135 incorporates a metallic object such as a catheter guiding wire 140. Because of the positioning of the heart 135 and thus wire 140 at the center or "focal point" of gantry 120, wire 140 is positioned at all times throughout the scan run between X-tray tube 130 and detector array 115 whilst gantry 120 rotates around wire 140. Because of the rigid arrangement in the gantry 120, x-ray tube 130 and detector 115 are at all times in opposite spatial relationship to each other. The CT scanner system 100 allows obtaining cross sectional slice images through the heart 135 and wire 140 through slice plane 125.

Figure 2:
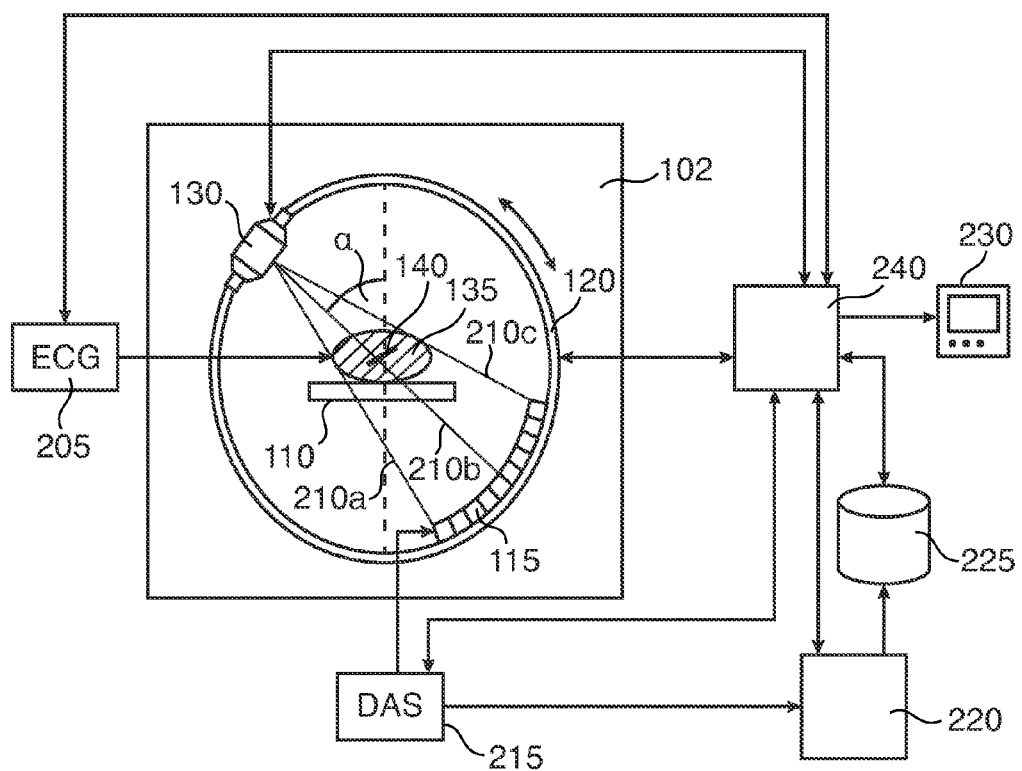
FIG. 2 shows a more detailed view of the CT scanner system of FIG. 1 in side elevation.

FIG. 2 affords a sectional view of scanner 100 in side elevation and in plan-view on slice image plane 125. CT scanner system 100 further comprises a workstation 240 to control operation of scanner 100, a data acquisition system (DAS) 215, an image reconstructor 220 and database 225 for holding the obtained slice images. The slice images may be retrieved from database 225 and rendered by workstation 240 for view on screen 230.

As gantry 120 rotates around heart 135, a series of projection images at different projection angles α ("alpha") is acquired, each image acquired at different times during gantry rotation as gantry 120 rotates in angle intervals from angle alpha to angle β ("beta").

Figure 3:
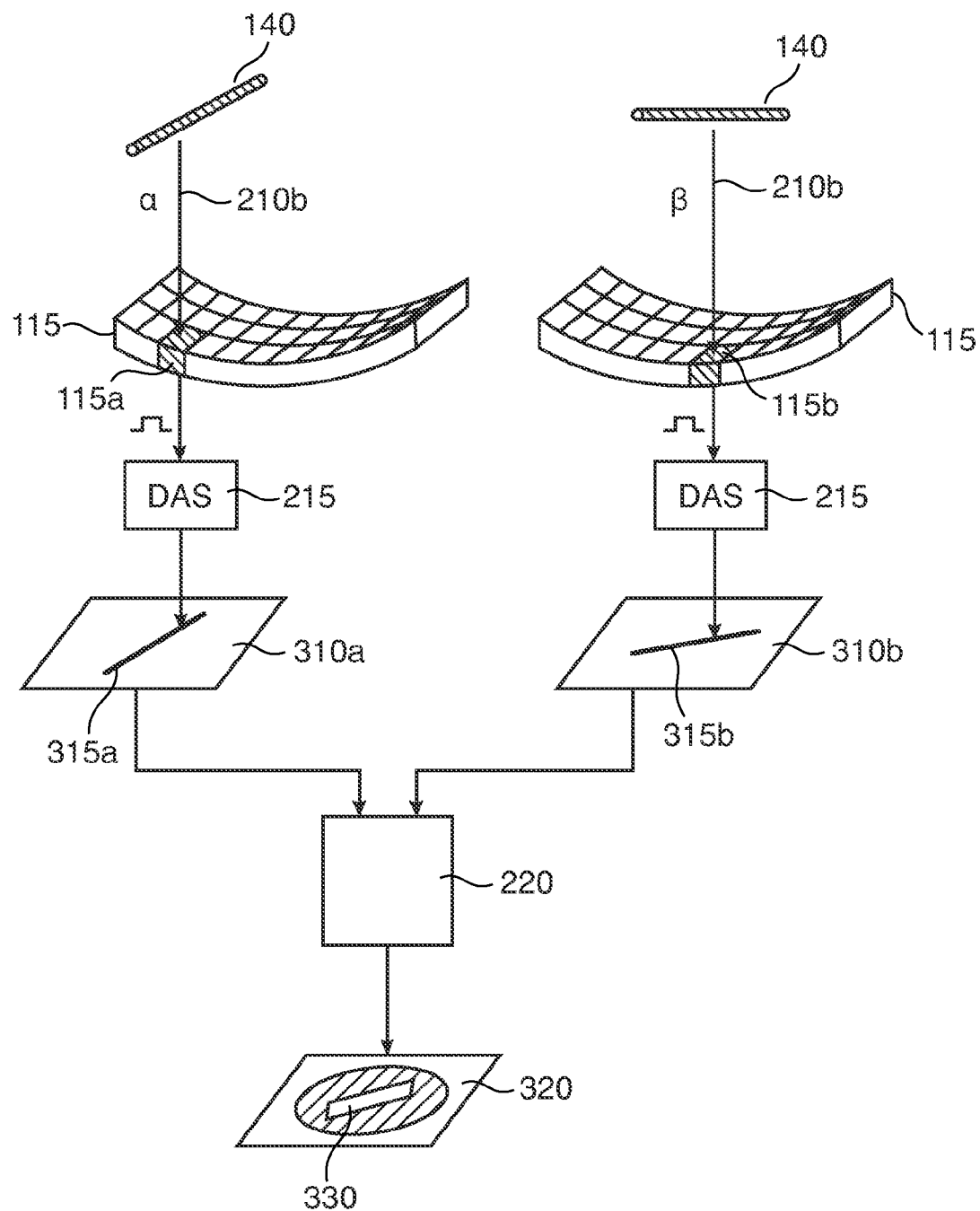
FIG. 3 shows operation of a CT slice image reconstructor.

In image acquisition operation, x-ray source 230 projects a fan beam of x-rays onto detector 115 at the opposite side of gantry cylinder 120. Fan beam of X-rays is formed of a collection of individual x-ray pencil beams 210a-c. Pencil beams 210a-b are emitted from x-ray source 130 at an initial intensity. Pencil beams 210a-c are attenuated as they pass through heart 135 and the so attenuated pencil beams egress heart 135 at its opposite side and are then incident on detector array 115. Detector array 115 is formed of detector elements. An exemplary detector element 115a is shown in FIG. 3.

Each detector element 115a generates an electric current inversely proportional to the attenuation experienced by the x-ray pencil beam incident on that detector element 115a. The current is then picked up and received at DAS 215 and converted by a suitable A-D conversion into a numerical digital value. The collection of digital values ("detector raw data") for each detector element 115a are then recorded in a matrix structure forming a digital projection image 310a,b, one projection image 310a or 310b for each projection angle alpha or beta. The row and column position i,j ("pixel") in the matrix corresponds to the row and column position i,j of the respective detector element 115a in the detector array 115. For each projection image 310a,b its acquisition time and projection angle is registered and the sequence of projection images 310a,b are then either stored in database 225 and/or are forwarded to image reconstructor 220.

Image reconstructor 220 uses known image reconstruction algorithms based on the inverse Radon transformation to produce a slice image 320 showing a cross section through image section plane 125 of heart 135 with wire 140. In other words, slice image 320 is the product of the inverse Radon transformation (or one of its many numerical implementations) applied to the sequence of projection images 310a,b, one for each projection angle alpha, beta. The so reconstructed slice image 320 can then be stored in database 225.

Because catheter wire 140 has a higher x-ray attenuation co-efficient than surrounding soft tissue, x-ray pencil beam 210b passing through wire 140 is attenuated more than x-ray pencil beams 210a,c not passing through wire 140 but through the surrounding heart soft tissue. As the heart is going through its cardiac cycles, motion is imparted on in-situ wire 140.

In the CT system shown in FIG. 2, a cardiac prospective gating imaging scheme is employed. To better image the heart when in a specific heart cycle phase suitable electro-cardio-equipment 205 is used. Electrode pads attached to the patient's chest around the heart region pick-up electric signals indicative to the current cardiac cycle phase. When an electric signal corresponding to the desired heart phase (for example systole or diastole) is sensed, a corresponding control command is then issued from ECG 205 to workstation 240 which in turn controls pulsing on or off x-ray tube 130 to acquire a projection image "snapshot" just at the right time when the heart is in the desired heart phase. In this way, the projection images 310a,b are acquired for each projection angle alpha at the desired cardiac phase and severe image artifacts caused by heart motion can be at least partly avoided because X-ray source 130 is pulsed off when heart is not in the targeted (resting) cardiac cycle or phase. Slight motions of wire 140 do still remain however, as gantry 120 moves from one projection angle to another because of delays in the pulsing on and off the X-ray tube 130 and other imperfections of the prospective gating procedure.

With reference to FIG. 3, the operation of CT scanner 100 as wire 140 changes its position because of heart motion activity is explained in more detail. Left portion of FIG. 3 shows the position of wire 140 (for clarity of exposition, the surrounding heart tissue is not shown) at a time when projection image 310a is acquired at projection angle alpha. The proportional electric signal generated by element 115a upon excitation by incident x-ray pencil beam 210b is then forwarded to DAS 215 where projection image 310a for angle alpha is being composed by registering each A-D-converted signal for each one of the detector elements. Because wire 140 has a higher attenuation co-efficient than the embedding heart tissue, a wire footprint 315a on the digital projection image 310a is formed or "imprinted".

During the time it takes for gantry 120 to rotate to next acquisition angle beta, the position of wire 140 has changed as shown on top and to the right in FIG. 3. As gantry 120 rotates from one projection angle alpha to next projection angle beta, wire 140 assumes different positions at different acquisition times.

In consequence, footprint 315b in second projection image 310b is different from footprint 315a in the previous projection image 310a acquired at projection angle alpha. The plurality of projection images 310a,b so obtained, each showing a footprint 315a,b or pixel value imprint of wire 140's true position at the respective projection image acquisition time and projection angle, are then fed into image reconstructor 220. Image constructor 220 inverse Radon transforms by projection the sequence of projection images 310a, b into the cross sectional slice image 320 representing the cross section of heart 135 through slice image plane 125. Because wire 140 has changed its position across the acquisition epoch, the reconstructed image region representative of wire 140 presents as a blurred image artifact 330 surrounding said image region. The true image boundary of the wire 140 in the image may be indiscernible even for the medically trained eye. The artifact is formed of a "metal shadow" smeared out across and around the image region representing the reconstructed wire in the slice image. The artifact 330 is schematically shown in FIG. 3. As a result of motion-caused blur and distortions, artifact 330 corresponding to the wire 140 is shown much thicker than the actual thickness of wire footprints 315a, b in the respective projection images 310a,b.

Figure 4:
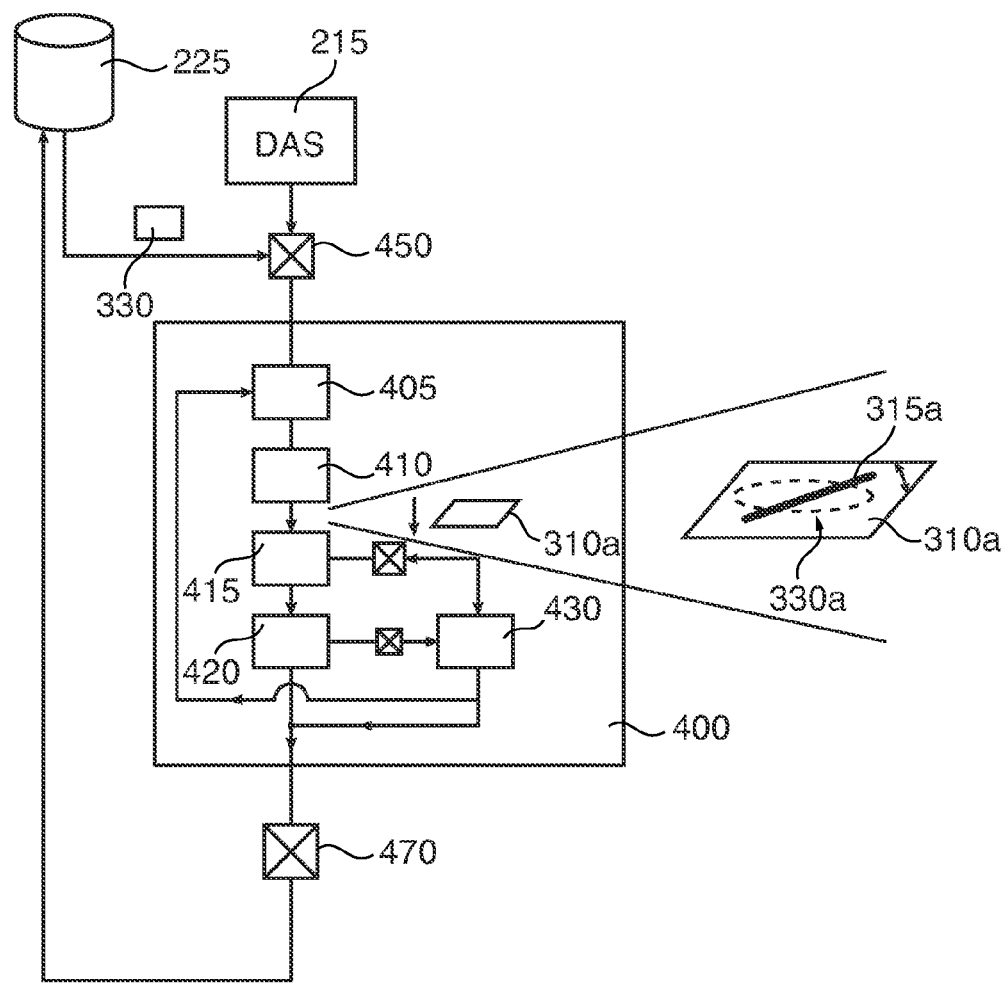
FIG. 4 shows an apparatus for correcting a cross sectional slice image for an image artifact according to an embodiment of the present invention.

FIG. 4 shows one embodiment of a slice image correction apparatus. The apparatus comprises an input unit or input interface means 415 and an output unit or output interface means 470. Apparatus 400 further comprises a processing unit 400 including a segmentor 405, an identifier 410, a matcher 415, and an interpolator 420. There is also an image reconstructor 430 that can receive output signals from matcher 415 or interpolator 420. Interface means 450 allows interfacing with DAS 215 or data base 225 to retrieve the to-be-corrected because artifact-laden image 330. Interface means 450 is also configured to access the plurality of projection images 310a, b which have been previously used by CT image reconstructor 220 to reconstruct slice image 330 having the artifact 330.

The apparatus components 450, 405, 410, 415, 420, 430 and 470 are running as software routines on processing unit 400. However, a distributed architecture of the apparatus where all the components are connected in a suitable communication network is also contemplated in alternative embodiments. The components may also be arranged as dedicated FPGAs or hardwired standalone chips. The components may be programmed in a suitable scientific computing platform such as Matlab® or Simulink® and may then be translated into for, example, C++ or C routines maintained in a library and linked when called on by processing unit 400.

Broadly speaking, apparatus 400 receives at interface means 450 slice image 320 having image artifact 330 and projection images 310a,b previously used for reconstruction of slice 320. Based on CT projection images 310a, b, slice image 320 is processed and an artifact corrected slice image is output at output means 470. The corrected image has either the representation of the metallic wire removed including the artifact caused by wire 140 motion during CT acquisition or the representation of the metallic wire is improved because it is shown at higher contrast with artifacts reduced. In one embodiment, the apparatus is also configured to iteratively improve, upon user request, the representation of the artifact shown in image 330 by producing in a pre-processing step, a new slice image showing the artifact less blurred than in initial slice 320. The improved artifact slice image may then be reviewed by a user and once approved, it is that newly pre-processed artifact slice image which is then fed back into segmenter 405 and processed by processing unit 400 to produce the corrected slice image.

Operation

Slice image 320 having artifact 330 is received at input means 450 and is forwarded to segmentor 405 and the location in storage 225 of projection images 310a,b is established to enable access of processing unit 400 to said projection images 310a,b.

Segmentor 405 segments image artifact 330 by using known segmentation techniques such as grey value intensity threshold segmentation. Each voxel whose grey value exceeds a predetermined and configurable threshold grey value is flagged up and considered to form part of image artifact region 330 and/or the image region representing metal part 140. The threshold segmentation can be used because metal wire 140 has a higher x-ray attenuation co-efficient than the surrounding organic material of the heart tissue and the image artifact region 330 including the region representing wire 140 will appear darker (or lighter depending on the color coding used for the slice image 320) than the remainder of the image. Because wire 140 is assumed to be moving during the acquisition epoch of the projection images 310a,b used for the previous image reconstruction of image 330, the artifact region can be thought of an image representation of a mean position of wire 140 during the acquisition epoch. In other words, the artifact may be considered the result of a superposition of the true positions of wire 140 at any one of the individual acquisition times of the respective projection images 310a, b. A segmentation data structure encoding the positions in the slice of those voxels which were established by segmentor 405 to belong to artifact region 330 are then forwarded to identifier 410.

Identifier 410 may be implemented as a forward projector, that is, a numerical implementation based on the Radon transformation. Identifier 410 then uses the segmentation data structure to forward project onto each of the projection images 310a, b the voxels making up the segmented artifact region 330. The region of pixels in each of the projection images 310a,b forming the image, in a mathematical sense, of the forward projection as applied to the segmented artifact region identifies a footprint of the artifact region in each of the projection image 310a,b. If F is the forward projection function and S is the voxel set in the slice plane forming the artifact region, then the artifact region 330 footprint is the image F(S) of the function F. The identification can be implemented by bit masks restricting the action of the forward projection to voxels inside the segmented artifact region 330. In this way the artifact region can be made to correspond to footprints in each one of projection images 310a,b although the artifact region in and of itself exists only in slice 320 as a result of the previous image reconstruction by CT image reconstructor 220. The so identified pixel regions in each of the CT projection images 310a,b constitute a footprint, one for each projection image 310a,b, of slice artifact region 330. A footprint 330a of artifact 330 is exemplary shown for projection image 310a in FIG. 3. The CT projection images 310a,b and a suitable data structure flagging up pixels making up the respective identified artifact region footprints are then forwarded to a matcher 415.

In each projection image 310a,b, matcher 415 matches up the artifact region footprint (330a for image 310a) to the respective true wire footprint 315a,b in that projection image 310a,b. Because the artifact region in the slice image is thought of as representation of the mean position and mean shape of the true wire positions and shape (in projection view) of wire 140, the overall shape of the artifact region footprint can be expected to be similar to the true footprints 315a,b in each of the projection images 310a,b.

Matcher 415 may be configured to implement the block-matching algorithm to scan each of the projection images 310a, b to match up the identified artifact region with the wire footprint 315a,b in the respective projection image 310a,b. Matcher 415 uses a selectable similarity measure to match for and in each projection 310a,b the shape of artifact footprint in that projection image to the shape of the respective wire footprint 315a or b as present in the respective projection image 310a or b, respectively. For example, with respect to the wire 140, its artifact footprints (for example 330a) as identified in each one of the projection images 310a, b are expected to have the shape of a curvilinear strip but, because of blurring, the strip will be broader than the likewise strip-shaped true wire footprints 315a,b The position of the artifact footprint relative to the position of the true wire footprint 315,a,b in the respective projection image 310a,b plane can be described by a vector and a matrix representing an in-plane rigid transformation. The transformation, when applied to the true wire footprint 315a would result in the wire footprint 315a to substantially coincide (up to the similarity measure) with the wire artifact region footprint 330a. Same applies, for each of the other projection images 310ab, to each of the other footprints 315b and the respective artifact region footprint 330b. The matching operation is schematically shown in FIG. 3 by the curved double arrow in the detailed view of projection image 310 to the right in FIG. 3. A coordinate description in a suitable data structure of the so matched true wire footprints 315a, b is then passed to interpolator 420.

Interpolator 420 then replaces the pixel values making up the true wire footprints 315a,b with interpolated values. Using the pixel region defined by footprints 315a,b as constraints for the interpolation, apparatus 400 can be user configured to completely average out the metallic wire part in the corrected slice or to generate a corrected slice showing the metallic wire at a higher contrast compared to the initial slice. If the metallic part is to be completely averaged out, the interpolator 420 uses average pixel information from outside each of the true wire footprints to so replace the pixel values inside wire footprint with the average pixel values.

According to one embodiment, interpolation is effected by averaging across lines straddling the wire footprint 315a, b in the projection image plane 310a,b. Initially, pixel values on the line to either side of the straddled footprint area 315a or 315b but outside the footprint area 315a or 315b are then averaged and used to replace pixel values on the line inside the footprint area 315a or 315b. Proceeding in a similar way along each of the lines by using moving averages along each of the lines, the pixel values inside the footprint area 315a or 315b are successively filled from the boundary of the footprint area towards its center, then also using previously interpolated pixel values inside the footprint area 315a or 315b, respectively.

If a representation of the metal wire in the final corrected slice image is to be preserved, interpolator 420 resets the pixel values inside the footprint to a level so as to improve the intensity/contrast as compared to the outside region in each of the projection images and correct for physical effects such as noise starvation and beam hardening. The so interpolated projection images are then forwarded to image reconstructor 430.

Reconstructor 430 implements the inverse operation to that of forward projector 410. Image reconstructor 430 reconstructs in a "second pass" (previous reconstruction at CT scanner system 100 of the initial slice 320 forming the "first pass") by backward projecting along straight lines the values from the interpolated projection images onto an image plane to so obtain the corrected slice image which is then output by output means 470 and forwarded for storage to database 225. Corrected image may then be rendered by a suitable graphic renderer for view on screen 230.

In one embodiment the apparatus is configured to provide a routine to improve the representation of the artifact region 330 itself by producing a new slice image which is then processed as previously described instead of the initial slice image. In other words the received slice image 330 is first pre-processed to produce a new slice image showing the artifact region at corrected contrast than the initial slice image and that new slice is then fed back into the apparatus to segmenter 205 and is processed in the sequence described above in relation to initial slice. Generating an improved slice image in this manner can be iterated until a satisfactory slice image is obtained showing the artifact to the expected standard with less blurs.

If a new slice image is requested, matcher 415 forwards the projection images 310a,b with the marked up matched wire footprints 315a,b to reconstructor 430 rather than passing the projection images 310a,b to interpolator 420 as previously described. Reconstructor 430 then uses the marked up true wire footprints 315a,b found by matcher 415 to compensate for wire 140 motion during acquisition of the projection images 310a,b. Reconstructor 430 effects compensation by registering the projection images 310a,b along a common coordinate system and by arranging the CT projection images 310a,b according to their acquisition time.

Reconstructor 430 then traces the apparent motion of footprints 315a,b from the earliest projection images through to the latest projection image by using the previously registered rigid transformations describing the apparent motion of the wire footprints relative to the previous artifact region footprint 330. The so traced motion is then used in the Radon transformation implemented by reconstructor 430 when reconstructing the improved slice image from the projection images 310a,b.

Rather than using straight lines for the Radon transformation based reconstruction, reconstructor 430 uses instead lines curved according to the traced motion to offset for said motion in the backward projection, thereby effecting the second pass motion compensation. In another embodiment, reconstructor 430 back-projects along straight projection lines but shifts each of the projection images according to the motion to thereby likewise effect the second pass motion compensation. In one embodiment, the rigid transformations previously established by matcher 415 are used for the line curving and image plane shift operations. The so reconstructed slice image will then show the artifact region less blurred. The user can then review the new slice after rendering on screen 230 for whether the now displayed artifact region is to his satisfaction and if not, the new slice is then feed back to segmenter 405, processed as previously described and passed on by matcher 415 to image reconstructor 430 to so iteratively generate further improved slice images. Once the user is satisfied with the improved slice image, the slice image is then processed as previously described and passed on to interpolator 420 by matcher 415 and subsequently output as the final corrected image.

The pre-processing may also be used as standalone without interpolation to merely improve artifact representation, that is, to remove excessive blur. Interpolator 420 is then skipped and the second pass motion compensated reconstructed slice is directly forwarded to output unit 470. In this case the improved slice is the final output when apparatus operates in this blur-reducing-only mode.

Figure 5:
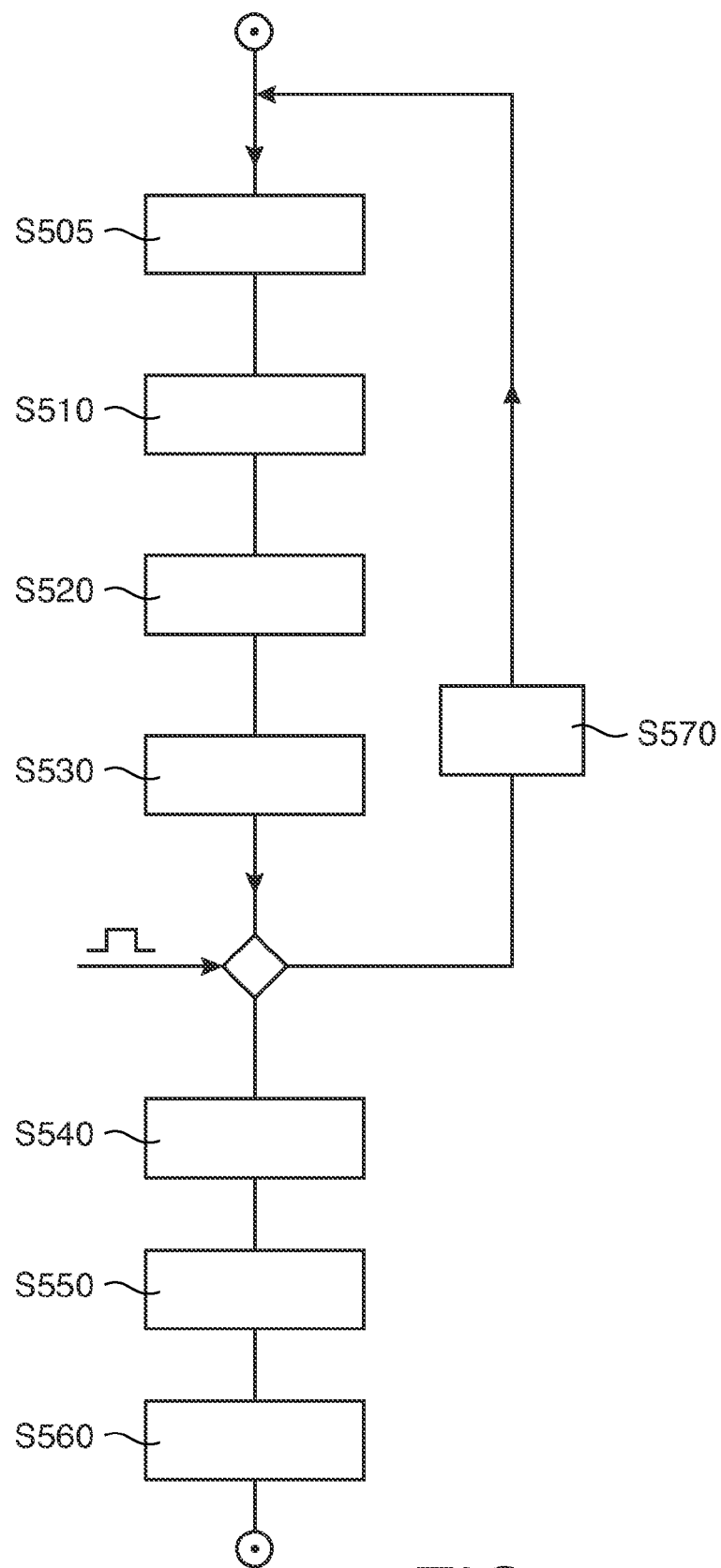
FIG. 5 shows a flow chart of a method for correcting a cross sectional slice images for an image artifact according to an embodiment of the present invention.

With reference to FIG. 5, a flow chart is shown for a method of correcting cross sectional slice images for an image artifact 330.

At step S505, slice 320 and projection images 310a,b or file references to the later are received.

At step S510 the slice image is segmented to obtain a segmented artifact region.

In step S520 the segmented artifact region is used to identify in each of a plurality of the projection images a footprint corresponding to the artifact region.

In step S530, for each of the plurality of the projection images, the identified footprint in the respective CT projection images is matched to a matching footprint in that CT projection image. The matching footprint represents the metal part's position at acquisition time of the respective CT projection image.

In step S540, for each of the plurality of the CT projection images, image information is interpolated using the image area enclosed by the matching footprint as a constraint for the interpolation in that CT projection image. The interpolation results in a plurality of interpolated CT projection images.

In step S550 the plurality of so interpolated CT images is then second pass reconstructed to obtain a corrected version of the slice image.

In step S560 the so reconstructed slice is then output as the corrected version of the slice image.

In one embodiment, the method further includes an optional step S570, carried out before above steps S540 and S550 are executed. In step S570, the reconstruction of the new slice image uses the matching footprints in the projection images, to thereby compensate for the part's motion during the acquisition of the CT projection images.

In one embodiment, the new slice reconstructed in step S570 is directly passed on to step S560 as the final output.

It is understood that in the above the wire is used as an example for a high attenuation part in a comparably low attenuating surrounding. The described apparatus can also be used for any other part, metallic or not, embedded in an object of any kind or standalone, that is moving during a CT scan.

According to one embodiment, the reconstructor traces the matching footprints across the plurality of projection images to trace the motion of the object during acquisition of the projection images. The traced motion is then accounted for in the reconstruction of the new slices.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for correcting across sectional slice image for an image artifact, the slice image based on computed tomography (CT) projection images taken of an object at different times and taken whilst a high-attenuation part of the object is in motion, the artifact caused by said motion, the apparatus comprising:

an input unit configured to receive the slice image and to access the plurality of CT projection images;

a processing unit with a processor comprising:

a segmenter configured to segment in the slice an artifact region;

an identifier configured to use the so segmented artifact region to identify in each of a plurality of the CT projection images a footprint corresponding to the artifact region;

a matcher configured to match, in each of the plurality of CT projection images, the identified footprint in the CT projection image to a matching footprint in that CT projection image, the matching footprint representing the part's position at acquisition time of that CT projection image;

an image reconstructor configured to reconstruct upon user requests a new slice image based on the plurality of matching footprints, thereby compensating for the part's motion during acquisition of the CT projection images, the segmenter, identifier and matcher then processing said new slice image instead of the slice image; and an interpolator configured to generate, for each of the plurality of CT projection images, an interpolated CT projection image by using the matching footprint in the CT projection image as a constraint for the interpolation in that CT projection image to so obtain a plurality of interpolated CT projection images, wherein the image reconstructor is further configured to use the plurality of interpolated CT projection images to reconstruct a corrected version of the slice image; and an output unit configured to output the corrected version of the slice image.

2. The apparatus of claim 1, wherein the plurality of interpolated CT projection images are generated by replacing, in each of the plurality of CT projection images, image information inside the matching footprint in that CT projection image by interpolated image information.

3. The apparatus of claim 1, the reconstructor configured to trace the matching footprints across the plurality of the CT projection images to so trace the part's motion and configured to use the traced motion for the reconstruction of the new slice, thereby effecting the motion compensation.

4. The apparatus of claim 1, wherein the identifier is implemented as a forward projector to forward project the artifact region onto each of the plurality of CT projection images thereby identifying the footprint of the artifact region; and
the matcher is implemented by using an image registration algorithm.

5. The apparatus of claim 1, wherein the artifact region in the slice image or in the new slice image represents a mean position over time of the part during its motion and whilst the CT projection images are acquired, the artifact region being the result of a previous reconstruction from the CT projection images of the slice image or the new slice image.

6. The apparatus of claim 1, wherein the object is a human or animal heart and the CT projection images are acquired by a prospectively gated cardiac CT scanner and the displacement of the part occurs inside the image acquisition gating window.

7. The apparatus of claim 1, wherein the part is metallic and from a group consisting of: an artificial valve, a bi-ventricular pacemaker, stent, a wire guide for stent introduction, and an Amplatzer device.

8. A medical image processing system for correcting a cross sectional slice image for an image artifact, the slice image based on CT projection images taken of an object at different times and angles relative to the object and taken whilst a high-attenuation part in or of the object is in motion, the artifact caused by said motion, the system comprising:
an apparatus of claim 1;
a database system holding the slice image and the CT projection images.

9. A method of correcting a cross sectional slice image for an image artifact, the slice image based on CT projection images taken of an object at different times and taken whilst a high-attenuation part of the object is in motion, the artifact caused by said motion, the method comprising a processing step including:
receiving the slice image and the plurality of CT projection images;
segmenting in the slice an artifact region;
using the so segmented artifact region for identifying, in each of a plurality of the CT projection images, a footprint corresponding to the artifact region;
in each of the plurality of CT projection images, matching the identified footprint in the CT projection image to a matching footprint in that CT projection image, the matching footprint representing the part's position at acquisition time of that CT projection image;
upon user request, generating a new slice image by reconstructing, based on the plurality of matching footprints, the new slice image, thereby compensating for the part's motion during acquisition of the CT projection images,
repeating the previous steps to the newly reconstructed and motion compensated slice image instead of the previous slice image;
for and in each of the plurality of CT projection images, interpolating and using the matching footprint in the respective CT projection image as a constraint for the interpolation to so obtain a plurality of interpolated CT projection images;
using the plurality of interpolated CT projection images for image reconstructing a corrected version of the slice image; and
outputting the corrected version of the slice image.

10. The method of claim 9, wherein the plurality of interpolated CT projection images are generated by replacing, in each of the plurality of CT projection images, image information inside the matching footprint in that CT projection image by interpolated image information.

11. The method of claim 9, wherein the reconstructing step as applied to the new slice image includes tracing the matching footprints across the plurality of the CT projection images to so trace the part's motion and using the traced motion in the reconstruction step for the new slice, thereby effecting the motion compensation.

12. A computer program element, stored on a non-transitory computer readable medium, for controlling an apparatus, which, when being executed by a processing unit is adapted to perform the method steps of claim 9.

13. A non-transitory computer readable medium having stored thereon the program element of claim 12.

14. A system, comprising:
a processor that matches, in each of a plurality of computed tomography (CT) projection images, an identified footprint in a CT projection image to a matching footprint in that CT projection image, wherein the plurality of CT projection images includes images of the object at different times, wherein the matching footprint represents a position of a high-attenuation part of an object, and wherein the high-attenuation part is in motion,
wherein the processor further reconstructs, upon request, a slice image based on the plurality of matching footprints, thereby compensating for the motion during acquisition of the CT projection images;
wherein the processor further generates, for each of the plurality of CT projection images, an interpolated CT projection image by using the matching footprint in the CT projection image as a constraint for the interpolation in that CT projection image to so obtain a plurality of interpolated CT projection images;
wherein the processor further reconstructs a corrected slice image based on the plurality of interpolated CT projection images; and
wherein the processor outputs the corrected slice image to a display device.

15. The system of claim 14, wherein, prior to the matching, the processor further segments an artifact region in an initial slice image and identifies the footprints, which correspond to the artifact region.

16. The system of claim 14, wherein the plurality of interpolated CT projection images are generated by replacing, in each of the plurality of CT projection images, image information inside the matching footprint in that CT projection image by interpolated image information.

17. The system of claim 14, wherein the processor further traces the matching footprints across the plurality of the CT projection images which traces the motion and the processor further uses the traced motion for the reconstruction of the slice.

18. The system of claim 14, wherein the processor further forward projects the artifact region onto each of the plurality of CT projection images to identify the footprint of the artifact region and matches the footprints using an image registration algorithm.

19. The system of claim 14, wherein artifact region in the slice image represents a mean position over time of the part during its motion.

20. The system of claim 14, wherein the part is metallic.

* * * * *